US00PP30013P3

(12) United States Plant Patent
Cain

(10) Patent No.: US PP30,013 P3
(45) Date of Patent: Dec. 25, 2018

(54) GRAPEVINE NAMED 'IFG TWENTY-SIX'

(50) Latin Name: *Vitis vinifera*
Varietal Denomination: IFG Twenty-six

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/530,100

(22) Filed: Dec. 6, 2016

(65) Prior Publication Data

US 2018/0160587 P1 Jun. 7, 2018

(51) Int. Cl.
*A01H 5/08* (2018.01)
*A01H 6/88* (2018.01)

(52) U.S. Cl.
USPC ..... Plt./205
CPC ..... *A01H 5/08* (2013.01); *A01H 6/88* (2018.05)

(58) Field of Classification Search
USPC ..... Plt./205
CPC ..... A01H 5/0812; A01H 5/08; A01H 5/00; A01H 5/02; A01H 6/88
See application file for complete search history.

(56) References Cited

PUBLICATIONS

Upov International Union for the Protection of New Varieties of Plants Grapevine Guidelines for the Conduct of Tests for Distinctness, Uniformity and Stability TG/50/9, 2008 pp. 1-5. (Year: 2008).*

* cited by examiner

*Primary Examiner* — June Hwu

(57) ABSTRACT

This invention is a new and distinct grapevine variety denominated 'IFG Twenty-six'. The new grapevine is characterized by producing large size elliptic to obtuse ovate fully black berries having medium firm texture with a neutral flavor and which ripen in early season. Berries are borne on large size clusters which are slightly compact and may require gibberellin applications to thin clusters and increase berry firmness.

1 Drawing Sheet

Latin name of the genus and species claimed: *Vitis vinifera.*

Variety denomination: 'IFG TWENTY-SIX'.

BACKGROUND OF THE INVENTION

The new and distinct grapevine described and claimed herein originated from a hand pollinated cross of 'IFG Thirteen' (U.S. Plant Pat. No. 24,466) and 'IFG 31-077' (U.S. Plant Pat. No. 20,292) hybridized in May 2006. The abortive seed traces were subsequently embryo cultured and the resulting 48 plants were planted in the field in April 2007. The present variety of grapevine was selected as a single plant in June 2008 and was first asexually propagated by hardwood cuttings in December 2008 near Delano, Kern County, Calif. These resulting cuttings produced second generation plants that were planted during April 2009 near Delano, Kern County, Calif. and were observed for four years and found to he true-to-type.

BRIEF SUMMARY OF THE INVENTION

The new grapevine 'IFG Twenty-six' is characterized by producing large size elliptic to obtuse ovate full black berries having medium firm texture with a neutral flavor and which ripen in early season. Berries are borne on large size clusters which are slightly compact and may require gibberellin applications to thin clusters and increase berry firmness. Berries color very well. Berries store moderately well and retain their condition for up to four weeks in cold storage. To the inventor's knowledge, the known variety to which the new grapevine variety is most similar is the Fantasy Seedless variety (unpatented). 'IFG Twenty-six' differs from the 'Fantasy Seedless' by having larger natural berry size, firmer berries, stronger thicker stems and which ripen three weeks earlier. 'IFG Twenty-six' is somewhat similar to 'Sugrathirteen' (U.S. Plant Pat. No. 10,434) but differs from 'Sugrathirteen' by having larger natural berry size, by more easily attaining full black color and exhibiting less tendency to crack at the stylar end.

'IFG Twenty-six' differs from its maternal parent the 'IFG Thirteen' by ripening approximately two weeks earlier, having larger natural berry size and by having stronger more fully lignified stems. 'IFG Twenty-six' differs from its pollen parent the 'IFG 31-077' by having larger clusters, larger natural berry size, by being more productive and by having firmer berries.

BRIEF DESCRIPTION OF THE DRAWING

The accompanying photographic drawing in FIG. 1 illustrates in full color 'IFG Twenty-six', taken from a four-year-old vine. The photograph was taken outdoors with indirect lighting. The colors are as nearly true as is reasonably possible in a color representation of this type. A mature fruit cluster and mature leaves are represented in the middle of the drawing. A shoot tip with young leaves and tendrils can be seen on the right side of the drawing. Typical berries in cross section can be seen on the lower left portion of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-six' plants grown in the vicinity of Delano, Kern County, Calif. during 2014 and 2015, and is believed to apply to plants of the variety grown under similar conditions of soil and climate elsewhere:

VINE

General:
- *Vigor*.—Vigorous.
- *Density of foliage*.—Dense.
- *Productivity*.—Very productive, producing about 20 to 25 kg of fruit per vine.
- *Root stock*.—Own root.
- *Training method*.—Typically spur pruned leaving 2 bud spurs.

Trunk:
- *Trunk diameter of* 4-*year-old vines at* 30 *cm above the soil line*.—About 8.9 cm.
- *Shape*.—Medium thick.
- *Straps*.—Very long, continuous.
- *Surface texture*.—Medium rough texture.
- *Inner bark color*.—Greyed-orange: 165A.

SHOOTS

Young shoot:
- *Form of tip*.—Wide open.
- *Distribution of anthocyanin coloration of tip*.—Piping (striped).
- *Intensity of anthocyanin coloration of tip*.—Weak.
- *Density of prostrate hairs of tip*.—Sparse.
- *Density of erect hairs on tip*.—Absent.
- *Color*.—Yellow-green: 144A.

Woody shoot (mature canes):
- *Internode length*.—Very long, about 13.6 cm.
- *Width at node*.—About 1.3 cm.
- *Cross section*.—Circular.
- *Surface*.—Striate.
- *Main color*.—The following colors were observed: Greyed-orange: 166A and 166B and 166C and 166D.
- *Density of erect hairs on nodes*.—None.
- *Density of erect hairs on internodes*.—None.
- *Axillary shoot length at full bloom*.—Short, approximately 4.1 cm.

Flowering shoot:
- *Vigor during flowering*.—Very strong.
- *Attitude during flowering on shoots not tied*.—Semi-drooping.
- *Color*.—Dorsal side of internodes — Yellow-green: 146C, with Red-purple stripes:59B.
- *Color*.—Ventral side of internodes — Yellow-green: 146C.
- *Color*.—Dorsal side of nodes — Yellow-green:146C, with Red-purple stripes:59B.
- *Color*.—Ventral side of nodes — Yellow-green:146C.
- *Density of prostrate hairs on nodes*.—Very sparse.
- *Density of erect hairs on nodes*.—None.
- *Density of prostrate hairs on internode*.—Very sparse.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Very long, about 29.5 cm.
- *Thickness of tendril* 2 *cm from base*.—About 3.7 mm.
- *Color*.—The following colors were observed: Yellow-green: 144A and Greyed-purple: 183C on dorsal sides of tendril.
- *Form*.—Bifurcated and trifurcated.
- *Number of consecutive tendrils*.—2.

LEAVES

Young leaves:
- *Color of upper surface of first four distal unfolded leaves*.—Yellow-green: 144A.
- *Color of lower surface of young leaves*.—The following colors were observed: Yellow-green: 146C and Greyed-orange: 176B.
- *Average intensity of anthocyanin coloration of six distal leaves prior to flowering*.—Absent.
- *Density of prostrate hairs between veins* (*lower surface*).—Very sparse.
- *Density of prostrate hairs on veins* (*lower surface*).—Very sparse.
- *Density of erect hairs between veins* (*lower surface*).—Absent.
- *Density of erect hairs on veins* (*lower surface*).—Very sparse.

Mature leaves:
- *Average length*.—About 13.1 cm.
- *Average width*.—About 18.8 cm.
- *Mature leaf size*.—Large.
- *Shape of blade*.—Wedge-shaped.
- *Number of lobes*.—5.
- *Blade venation*.—Palmate.
- *Anthocyanin coloration of main veins on upper side of blade*.—Medium.
- *Mature leaf profile*.—Undulate.
- *Blistering surface of blade upper surface*.—Very weak.
- *Leaf blade tip*.—In the plane of the leaf.
- *Undulation of margin*.—Medium.
- *Undulation of blade between main and lateral veins*.—Absent.
- *Shape of teeth*.—Mixture of both sides straight and both sides convex.
- *Length of teeth*.—Long.
- *Ratio length/width of teeth*.—Medium.
- *Shape of upper lateral sinuses*.—Closed.
- *Depth of upper lateral sinuses*.—Medium.

*General shape petiole sinus*.—Wide open.
*Shape of base of upper leaf sinuses*.—V-shaped.
*Tooth at petiole sinus*.—Absent.
*Density of prostrate hairs between veins on lower surface of blade*.—Absent.
*Density of erect hairs between veins on lower surface of blade*.—Absent.
*Density of prostrate hairs on main veins on lower surface of blade*.—None or very sparse.
*Density of erect hairs on main veins on lower surface of blade*.—Very sparse.
*Density of prostrate hairs on main veins on upper surface of blade*.—Very sparse.
*Density of erect hairs on main veins on upper surface of blade*.—None.
*Autumn coloration of leaves*.—Leaves can be a single color or combination of colors, in a mottled pattern on the edges of the leaves. The following colors were observed: Greyed-yellow: 162A and 162B and 163C, Greyed-purple: 184A and 187A, and Greyed-red: 181A and 181B.

Upper surface:
*Color*.—Green: 137A.
*Color of main veins*.—The following colors were observed: Yellow-green: 145B and Greyed-red: 182B.
*Anthocyanin coloration of main veins (lower surface)*.—Medium.
*Surface appearance*.—Semi-glossy.
*Blistering surface of blade*.—Very weak.

Lower surface:
*Color*.—The following colors were observed: Yellow-green: 146A and 146B.
*Color of main veins*.—Yellow-green: 145B.
*Anthocyanin coloration of main veins (lower surface)*.—Medium.
*Glossiness*.—Weak.
*Surface texture*.—Smooth.
*Surface appearance*.—Dull.

Petiole:
*Length*.—About 13.1 cm.
*Length of petiole compared to middle vein*.—Equal.
*Diameter of petiole 2 cm from blade*.—About 3.3 mm.
*Petiole color*.—The following colors were observed: Yellow-green: 145B and Greyed Red: 182B.
*Density of prostrate hairs on petiole*.—None.
*Density of erect hairs on petiole*.—None.

Buds:
*Bud fruitfulness*.—Basal: mostly fruitful.
*Position of first fruitful shoot on previous season cane*.—$1^{st}$ to $3^{rd}$ node.
*Dormant bud length*.—About 5.8 mm.
*Dormant bud width in the proximal/distal plane*.—About 5.9 mm.
*Dormant bud color*.—Greyed-orange: 166A.
*Time of bud burst*.—Midseason: about Mar. 5, 2016.

FLOWERS

General:
*Flower sex*.—Hermaphrodite.
*Length of single flower, unopened*.—About 4.0 mm.
*Width of single flower*.—Unopened — About 2.3 mm, opened: About 7.6 mm.
*Stamen length*.—About 3.2 mm.
*Stamen count*.—5.
*Pollen color*.—Yellow: 10B.
*Pollen amount*.—Moderate.
*Pistil length*.—About 3.3 mm.
*Pistil color*.—Yellow-green: 144A.
*Length of first inflorescence*.—Long, about 21.3 cm long by 12.9 cm wide.
*Position of first flowering and fruiting node*.—$3^{rd}$ to $4^{th}$ node (current season growth).
*Number of inflorescence per flowering shoot*.—1.1 to 2: Average about 2.
*Time of bloom*.—Midseason as compared with similar varieties in the growing area of Delano, Calif.
*Date of full bloom*.—About May 4, 2016.

FRUIT

General:
*Ripening period*.—Early: approximately Jul. 15, 2015.
*Use*.—Fresh market.
*Keeping quality*.—Moderate, can be prone to berry shatter during handling and prolonged storage.
*Resistance to*.—Insects: Average typical of *Vitis vinifera* species. Diseases: Average typical of *Vitis vinifera* species.
*Refractometer test*.—Soluble solids: about 17.0 Brix.
*Brix/acid*.—About 50.0.
*Titratable acidity*.—About 0.34
*Juice ph*.—About 3.84.

Cluster:
*Mature cluster length (peduncle excluded)*.—About 24.9 cm.
*Mature cluster width*.—About 18.4 cm.
*Mature cluster weight*.—About 1085 g.
*Bunch density*.—Medium.
*Number of berries*.—About 167.
*Form*.—Conical.

Peduncle:
*Lignification of peduncle*.—Slight.
*Length of peduncle*.—Short to medium, approximately 3.8 cm.
*Peduncle color*.—Yellow-green: 145A.

Berry:
*Uniformity of size*.—Uniform.
*Single berry weight*.—About 7.0 g natural; to about 8.0 g when treated with gibberellic acid.
*Shape*.—Elliptic to slightly obtuse ovate.
*Seeds*.—Contains small rudimentary seed traces.
*Cross section*.—Circular.
*Berry dimensions*.—Longitudinal axis: about 3.1 cm; horizontal axis: about 2.0 cm.
*Berry firmness*.—Medium.
*Particular flavor*.—Neutral.
*Bloom (cuticular wax)*.—Medium strong.
*Berry separation from pedicel*.—Medium to easy.
*Skin color (without bloom)*.—Greyed-purple: N186A.
*Berry flesh color*.—Greyed-purple: N187D.
*Berry flesh anthocyanin*.—Weak.

Skin:
*Thickness*.—Medium thin.
*Skin toughness*.—Not notable when chewing.
*Reticulation*.—Absent.
*Tenacity*.—Tenacious to flesh.

What is claimed:

1. A new and distinct variety of grapevine as herein illustrated and described.

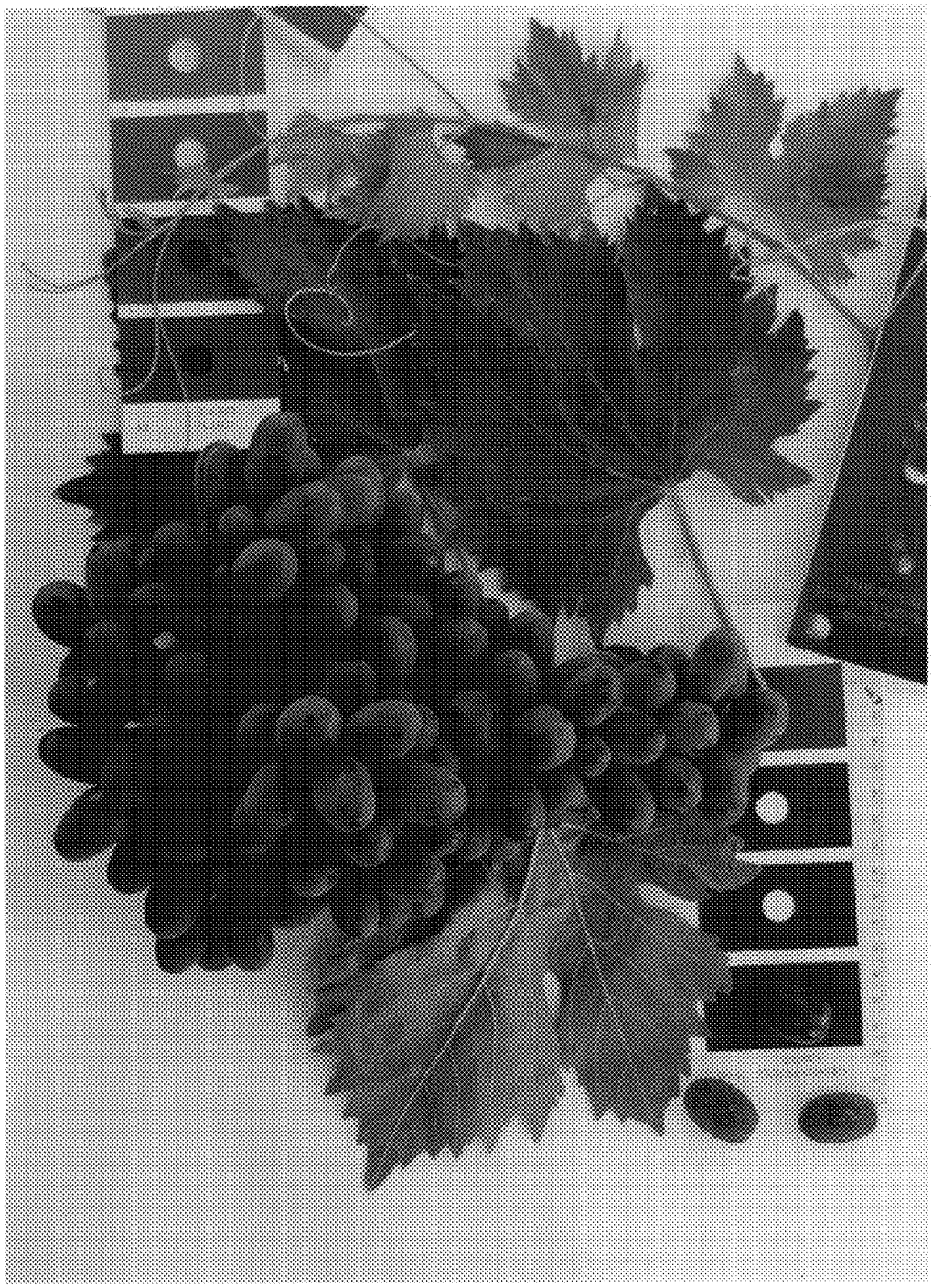

* * * * *